US012669625B2

(12) United States Patent
Xue et al.

(10) Patent No.: US 12,669,625 B2
(45) Date of Patent: Jun. 30, 2026

(54) SYSTEMS AND METHODS FOR CORRECTING POSITRON EMISSION TOMOGRAPHY DEVICES

(71) Applicant: SHANGHAI UNITED IMAGING HEALTHCARE CO., LTD., Shanghai (CN)

(72) Inventors: Manquan Xue, Shanghai (CN); Xinyu Lyu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 27 days.

(21) Appl. No.: 18/487,088

(22) Filed: Oct. 15, 2023

(65) Prior Publication Data

US 2024/0036222 A1 Feb. 1, 2024

Related U.S. Application Data

(63) Continuation of application No. PCT/CN2022/087102, filed on Apr. 15, 2022.

(30) Foreign Application Priority Data

Apr. 15, 2021 (CN) .......................... 202110405984.1

(51) Int. Cl.
*G01T 7/00* (2006.01)
*A61B 6/03* (2006.01)
(Continued)

(52) U.S. Cl.
CPC ................ *G01T 7/00* (2013.01); *A61B 6/037* (2013.01); *A61B 6/585* (2013.01); *G01T 1/202* (2013.01)

(58) Field of Classification Search
CPC ......... G01T 7/00; G01T 1/202; G01T 1/2985; A61B 6/037; A61B 6/585; A61B 6/4258; A61B 6/5205; A61B 6/582
See application file for complete search history.

(56) References Cited

U.S. PATENT DOCUMENTS

| | | | |
|---|---|---|---|
| 8,809,793 B2 | 8/2014 | Wagadarikar et al. | |
| 11,543,545 B2 | 1/2023 | Li et al. | |

(Continued)

FOREIGN PATENT DOCUMENTS

| | | |
|---|---|---|
| CN | 106539591 A | 3/2017 |
| CN | 107242881 A | 10/2017 |

(Continued)

OTHER PUBLICATIONS

Rothfuss et al., "Time Alignment of Time of Flight Positron Emission Tomography using the Background Activity of LSO", IEEE, 3 pages. (Year: 2013).*

(Continued)

*Primary Examiner* — Kiho Kim
(74) *Attorney, Agent, or Firm* — METIS IP LLC

(57) ABSTRACT

The present disclosure is related to systems and methods for data masking. The method includes obtaining data associated with coincidence events related to intrinsic background radiations of a plurality of crystals of the PET device. Each of the coincidence events may be detected by two crystals of the plurality of crystals of the PET device. The data associated with the each coincidence event may include first time information and second time information. The method includes determining a first time of fight (TOF) difference corresponding to the each coincidence event based on the first time information and the second time information. The method includes determining a second TOF difference corresponding to the each coincidence event based on locations of the two crystals that detect the each coincidence event.

(Continued)

The method includes correcting the PET device based on the first TOF difference and the second TOF difference.

20 Claims, 8 Drawing Sheets

(51) Int. Cl.
  *A61B 6/58*        (2024.01)
  *G01T 1/202*       (2006.01)

(56)                References Cited

U.S. PATENT DOCUMENTS

| | | | |
|---|---|---|---|
| 11,573,339 | B2 | 2/2023 | Li et al. |
| 11,644,586 | B2 | 5/2023 | Chen |
| 11,647,970 | B2 | 5/2023 | Miyahara |
| 11,675,097 | B2 | 6/2023 | Olcott et al. |
| 11,819,357 | B2 | 11/2023 | Sun et al. |
| 11,846,735 | B2 | 12/2023 | Solf et al. |
| 11,904,184 | B2 | 2/2024 | Maolinbay |
| 2006/0102845 | A1 | 5/2006 | Williams et al. |
| 2007/0152162 | A1 | 7/2007 | Griesmer et al. |
| 2008/0251709 | A1 | 10/2008 | Cooke et al. |
| 2011/0127413 | A1 | 6/2011 | Casey et al. |
| 2012/0121050 | A1 | 5/2012 | De Geronimo |
| 2012/0228484 | A1 | 9/2012 | Burr |
| 2013/0062526 | A1 | 3/2013 | Tsuda et al. |
| 2013/0087710 | A1 | 4/2013 | Zhang et al. |
| 2014/0217294 | A1 | 8/2014 | Rothfuss et al. |
| 2015/0285922 | A1 | 10/2015 | Mintzer et al. |
| 2015/0301201 | A1 | 10/2015 | Rothfuss et al. |
| 2015/0331119 | A1 | 11/2015 | Wang et al. |
| 2017/0276811 | A1 | 9/2017 | Wang |
| 2018/0214085 | A1 | 8/2018 | Sun et al. |
| 2018/0308261 | A1 | 10/2018 | Liu et al. |
| 2020/0072988 | A1 | 3/2020 | Cho et al. |
| 2023/0102139 | A1 | 3/2023 | Lyu et al. |

FOREIGN PATENT DOCUMENTS

| | | | |
|---|---|---|---|
| CN | 107411768 | A | 12/2017 |
| CN | 107507164 | A | 12/2017 |
| CN | 109259786 | A | 1/2019 |
| CN | 109709596 | A | 5/2019 |
| CN | 110179485 | A | 8/2019 |
| CN | 110211095 | A | 9/2019 |
| CN | 110288008 | A | 9/2019 |
| CN | 110584698 | A | 12/2019 |
| CN | 110749916 | A | 2/2020 |
| CN | 111012372 | A | 4/2020 |
| CN | 111568452 | A | 8/2020 |
| CN | 111568453 | A | 8/2020 |
| CN | 111685785 | A | 9/2020 |
| CN | 111714147 | A | 9/2020 |
| CN | 111728625 | A | 10/2020 |
| JP | 2009243998 | A | 10/2009 |
| WO | 2022218414 | A1 | 10/2022 |

OTHER PUBLICATIONS

International Search Report in PCT/CN2022/087102 mailed on Jul. 11, 2022, 5 pages.
Written Opinion in PCT/CN2022/087102 mailed on Jul. 11, 2022, 5 pages.
Shi, Hongcheng, PET/CT: Clinical Evidence-based Practice and Procedure Guidance, Shanghai Scientific and Technical Publishers, 2019, 9 pages.
The Extended European Search Report in European Application No. 22787636.4 mailed on Jul. 25, 2024, 10 pages.
International Search Report in PCT/CN2021/095840 mailed on Jul. 29, 2021, 10 pages.
Written Opinion in PCT/CN2021/095840 mailed on Jul. 29, 2021, 13 pages.
First Office Action in Chinese Application No. 202010448695.5 mailed on Aug. 26, 2021, 18 pages.
First Office Action in Chinese Application No. 202010448693.6 mailed on Aug. 26, 2021, 16 pages.
The Second Office Action in Chinese Application No. 202010448693.6 mailed on May 13, 2022, 19 pages.
First Office Action in Chinese Application No. 202010604518.1 mailed on Aug. 26, 2021, 16 pages.
First Office Action in Chinese Application No. 202010604531.7 mailed on Aug. 27, 2021, 14 pages.
First Office Action in Chinese Application No. 202010626175.9 mailed on Aug. 27, 2021, 15 pages.
Wei, Qingyang, Intrinsic Radiation in Lutetium Based PET Detector: Advantages and Disadvantages, Arxiv. 1501.05372, 2015, 10 pages.
The Extended European Search Report in European Application No. 21814520.9 mailed on Sep. 21, 2023, 17 pages.
Notice of Reasons for Rejection in Japanese Application No. 2024-102650 mailed on Mar. 11, 2025, 12 pages.

* cited by examiner

100

111

112

113

110

114

130

150

120

Storage
Device

Network

140

141          142          143

...

200

Processor
210

Storage
220

I/O
230

Communication
Port
240

300

Communication
Platform
310

Display
320

360

OS
370

App(s)
380

Memory

GPU
330

CPU
340

I/O
350

Storage
390

<u>500</u>

Obtaining data associated with coincidence events related to intrinsic background radiations of a plurality of crystals of a PET device, wherein each of the coincidence events is detected by two crystals of the plurality of crystals of the PET device, and the data associated with the each coincidence event includes first time information and second time information    510

Determining a first time of fight (TOF) difference corresponding to the each coincidence event based on the first time information and the second time information    520

Determining a second TOF difference corresponding to the each coincidence event based on locations of the two crystals that detect the each coincidence event    530

Correcting the PET device based on the first TOF difference and the second TOF difference    540

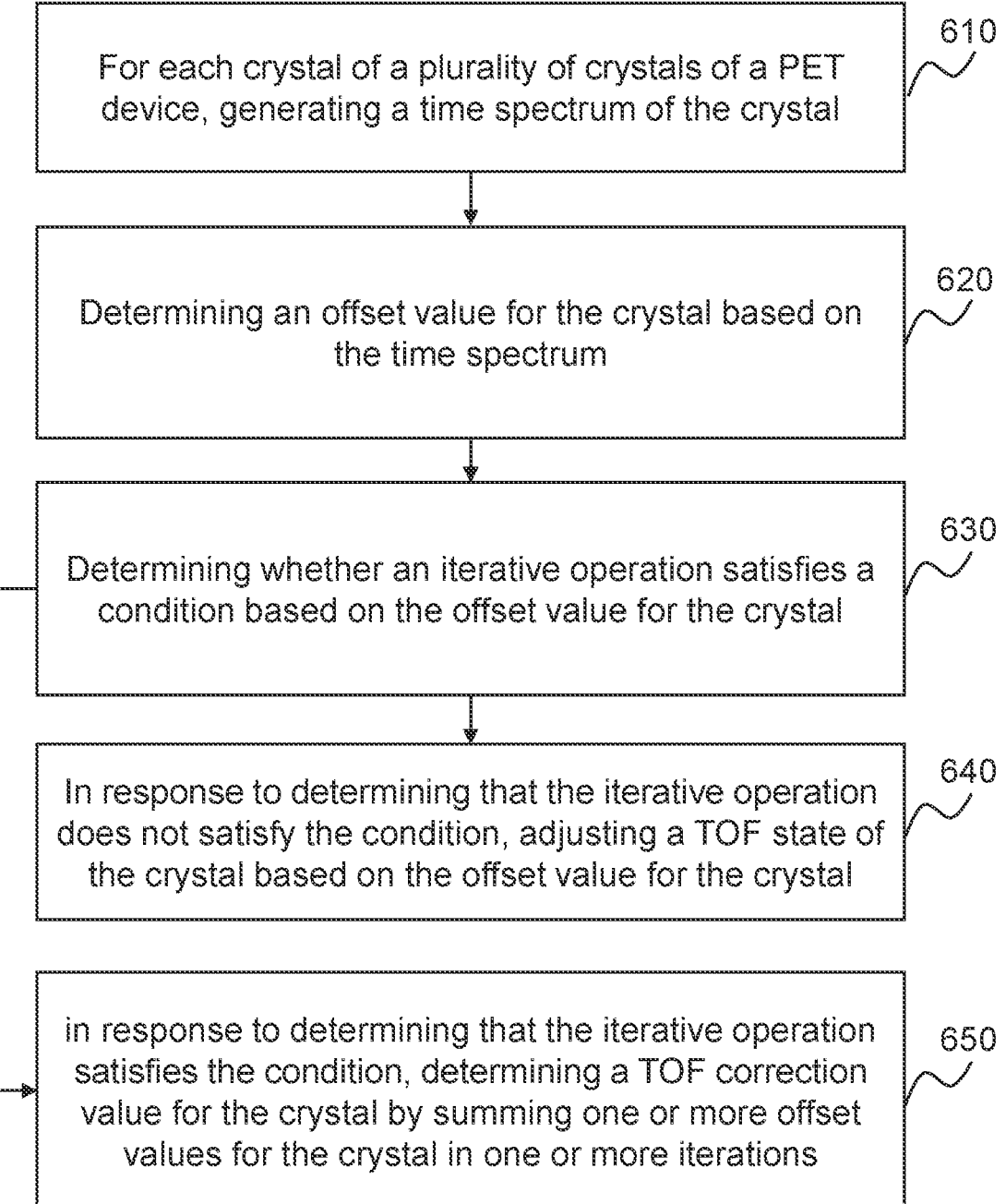

For each crystal of a plurality of crystals of a PET device, generating a time spectrum of the crystal          610

Determining an offset value for the crystal based on the time spectrum          620

Determining whether an iterative operation satisfies a condition based on the offset value for the crystal          630

In response to determining that the iterative operation does not satisfy the condition, adjusting a TOF state of the crystal based on the offset value for the crystal          640 in response to determining that the iterative operation satisfies the condition, determining a TOF correction value for the crystal by summing one or more offset values for the crystal in one or more iterations          650

FIG. 6

SYSTEMS AND METHODS FOR CORRECTING POSITRON EMISSION TOMOGRAPHY DEVICES

CROSS-REFERENCE TO RELATED APPLICATIONS

This application is a Continuation of International Application No. PCT/CN2022/087102, filed on Apr. 15, 2022, which claims priority of Chinese Patent Application No. 202110405984.1, filed on Apr. 15, 2021, and the contents of each of which are hereby incorporated by reference.

TECHNICAL FIELD

This disclosure generally relates to systems and methods for positron emission tomography (PET) devices, and more particularly, relates to systems and methods for correcting the PET devices.

BACKGROUND

Positron emission tomography (PET) has been widely used in medicine for diagnosis and other purposes. The accurate assessment of a disease of a patient relies on the accurate acquisition of PET data. However, due to the aging of components of the PET device and the influence of the external environment, a state (e.g., an energy state, a time of fight (TOF) state) of the PET device may be changed, which may affect the quality of the PET data obtained by the PET device. Traditionally, an extraneous radiation source may be introduced to correct the state of the PET device, which may cause unnecessary radiation to an operator, and increase the unavailability time of the PET device. Therefore, it is desirable to provide systems and methods for correcting the PET device accurately and efficiently.

SUMMARY

According to an aspect of the present disclosure, a method may be implemented on a computing device having one or more processors and one or more storage devices. The method may include obtaining data associated with coincidence events related to intrinsic background radiations of a plurality of crystals of the PET device. Each of the coincidence events may be detected by two crystals of the plurality of crystals of the PET device. The data associated with the each coincidence event may include first time information and second time information. The method may include determining a first time of fight (TOF) difference corresponding to the each coincidence event based on the first time information and the second time information. The method may include determining a second TOF difference corresponding to the each coincidence event based on locations of the two crystals that detect the each coincidence event. The method may include correcting the PET device based on the first TOF difference and the second TOF difference.

In some embodiments, the each coincidence event may include a β event and a γ event. The first time information may correspond to the β event, and the second time information may correspond to the γ event.

In some embodiments, the method may include, for the each coincidence event, obtaining a first optical signal excited by a β particle and a second optical signal excited by a γ particle. The method may include obtaining a first electric signal by converting the first optical signal. The method may include obtaining a second electric signal by converting the second optical signal. The method may include determining the first time information based on the first electric signal. The method may include determining the second time information based on the second electric signal.

In some embodiments, the method may include obtaining the data associated with the coincidence events based on a target energy window and a target time window. The target energy window may be determined based on at least one of a β particle energy, a γ particle energy, or a reference energy. The target time window may be determined based on a reference time.

In some embodiments, a first crystal of the two crystals may detect the β particle, and a second crystal of the two crystals may detect the γ particle. The method may include determining the second TOF difference based on a distance between the location of the first crystal and the location of the second crystal.

In some embodiments, the method may include determining the second TOF difference by dividing the distance between the location of the first crystal and the location of the second crystal by a speed of light.

In some embodiments, a first detector including the first crystal and a second detector including the second crystal may be spaced apart from each other.

In some embodiments, the method may include, for each crystal of the plurality of crystals of the PET device, generating a time spectrum based on the first TOF difference and the second TOF difference corresponding to each of one or more of the coincidence events detected between the crystal and other crystals. The method may include determining a TOF correction value based on the time spectrum. The method may include correcting the PET device based on the TOF correction value corresponding to the each crystal of the plurality of crystals of the PET device.

In some embodiments, the method may include determining the TOF correction value based on the time spectrum according to an iterative operation including one or more iterations. In at least one of the one or more iterations, the method may include, for the each crystal of the plurality of crystals of the PET device, generating a time spectrum of the crystal. The method may include determining an offset value for the crystal based on the time spectrum. The method may include determining whether the iterative operation satisfies a condition based on the offset value for the crystal. The method may include, in response to a result of determining whether the iterative operation satisfies the condition based on the offset value for the crystal, adjusting TOF information of the crystal based on the offset value for the crystal, or determining the TOF correction value for the crystal by summing one or more offset values for the crystal in the one or more iterations.

In some embodiments, the method may include recording the TOF correction value in a correction file of the PET device, or programming the TOF correction value in one or more detectors of the PET device.

In some embodiments, the method may include performing a time walk effect correction and/or a position correction on the first TOF difference.

In some embodiments, the method may include correcting the PET device based on energy information of the data associated with the coincidence events.

In some embodiments, the method may include generating a reference energy spectrum based on energy information of the each coincident event. The method may include determining a reference peak position in the reference energy spectrum. The method may include determining a target peak position based on the reference peak position in the reference energy spectrum. The method may include correcting energy information of the crystal of the PET device based on the target peak position and a corrected peak position.

In some embodiments, the method may include determining whether the energy information of the crystal of the PET device needs to be corrected based on the target peak position and the corrected peak position. The method may include, in response to determining that the energy information of the crystal of the PET device needs to be corrected, programming the target peak position in one or more detectors of the PET device.

In some embodiments, the method may include determining the target peak position based on the reference peak position and a relationship between a position of a peak and an energy of the peak.

According to another aspect of the present disclosure, a system may include at least one storage device storing a set of instructions, and at least one processor in communication with the at least one storage device. When executing the stored set of instructions, the at least one processor may cause the system to perform a method. The method may include obtaining data associated with coincidence events related to intrinsic background radiations of a plurality of crystals of the PET device. Each of the coincidence events may be detected by two crystals of the plurality of crystals of the PET device. The data associated with the each coincidence event may include first time information and second time information. The method may include determining a first time of fight (TOF) difference corresponding to the each coincidence event based on the first time information and the second time information. The method may include determining a second TOF difference corresponding to the each coincidence event based on locations of the two crystals that detect the each coincidence event. The method may include correcting the PET device based on the first TOF difference and the second TOF difference.

According to another aspect of the present disclosure, a non-transitory computer readable medium may include at least one set of instructions. When executed by at least one processor of a computing device, the at least one set of instructions may cause the at least one processor to effectuate a method. The method may include obtaining data associated with coincidence events related to intrinsic background radiations of a plurality of crystals of the PET device. Each of the coincidence events may be detected by two crystals of the plurality of crystals of the PET device. The data associated with the each coincidence event may include first time information and second time information. The method may include determining a first time of fight (TOF) difference corresponding to the each coincidence event based on the first time information and the second time information. The method may include determining a second TOF difference corresponding to the each coincidence event based on locations of the two crystals that detect the each coincidence event. The method may include correcting the PET device based on the first TOF difference and the second TOF difference.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 5 is a flowchart illustrating an exemplary process for correcting a PET device according to some embodiments of the present disclosure;

FIG. 6 is a flowchart illustrating an exemplary process for determining a TOF correction value according to some embodiments of the present disclosure;

DETAILED DESCRIPTION

Figure 1:
FIG. 1 is a schematic diagram illustrating an exemplary medical system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. Also, the term "exemplary" is intended to refer to an example or illustration.

It will be understood that the terms "system," "engine," "unit," "module," and/or "block" used herein are one method to distinguish different components, elements, parts, sections or assembly of different levels in ascending order. However, the terms may be displaced by another expression if they achieve the same purpose.

An aspect of the present disclosure relates to a system and method for correcting a PET device. According to some embodiments of the present disclosure, a processing device may obtain data associated with coincidence events related to intrinsic background radiations of a plurality of crystals of the PET device. Each of the coincidence events may be detected by two crystals of the plurality of crystals of the PET device. The data associated with the each coincidence event may include first time information and second time information. The processing device may determine a first time of fight (TOF) difference corresponding to the each coincidence event based on the first time information and the second time information. The processing device may determine a second TOF difference corresponding to the each coincidence event based on locations of the two crystals that detect the each coincidence event. The processing device may correct a TOF state of the PET device based on the first TOF difference and the second TOF difference.

Another aspect of the present disclosure relates to a system and method for correcting a PET device. According to some embodiments of the present disclosure, a processing device may obtain data associated with a single event or a coincidence event related to an intrinsic background radiation of a crystal of the PET device. The processing device may generate a reference energy spectrum based on energy information of the single event or the coincidence event. The processing device may determine a reference peak position in the reference energy spectrum. The processing device may determine a target peak position based on the reference peak position in the reference energy spectrum. The processing device may determine an energy correction state based on the target peak position and a corrected peak position. The processing device may correct an energy state of the PET device based on the energy correction state.

Accordingly, a state (e.g., a TOF state, an energy state) of a PET device may be corrected based on data associated with a single event or a coincidence event related to intrinsic background radiations of a plurality of crystals of the PET device without using an extraneous radiation source. The radiation dose received by an operator of the PET device may be reduced and a cost for PET device correction may be reduced.

FIG. 1 is a schematic diagram illustrating an exemplary medical system according to some embodiments of the present disclosure. As illustrated, the medical system 100 may include a medical device 110, a processing device 120, a storage device 130, a terminal 140, and a network 150. The components of the medical system 100 may be connected in one or more of various ways. Merely by way of example, as illustrated in FIG. 1, the medical device 110 may be connected to the processing device 120 directly as indicated by the bi-directional arrow in dotted lines linking the medical device 110 and the processing device 120, or through the network 150. As another example, the storage device 130 may be connected to the medical device 110 directly as indicated by the bi-directional arrow in dotted lines linking the medical device 110 and the storage device 130, or through the network 150. As still another example, the terminal 140 may be connected to the processing device 120 directly as indicated by the bi-directional arrow in dotted lines linking the terminal 140 and the processing device 120, or through the network 150.

In some embodiments, the medical device 110 may scan a subject, and acquire data relating to the subject. In some embodiments, the medical device 110 may be an emission computed tomography (ECT) device, a positron emission tomography (PET) device, a single photon emission computed tomography (SPECT) device, a multi-modality device, or the like, or any combination thereof. Exemplary multi-modality device may include a CT-PET device, an MR-PET device, or the like. In some embodiments, the multi-modality device may include modules and/or components for performing PET imaging and/or related analysis.

In some embodiments, the medical device 110 may be a PET device including a gantry 111, a PET detector 112, a detection region 113, and a table 114. The PET detector 112 may detect radiation events (e.g., γ photons) emitted from the detection region 113. In some embodiments, the PET detector 112 may include a plurality of detectors. The PET detector 112 may be and/or include a single-row detector in which the plurality of detectors are arranged in a single row and/or a multi-row detector in which the plurality of detectors are arranged in multiple rows. In some embodiments, each detector of the plurality of detectors may include a crystal (e.g., a scintillator), a light guide, and a photoelectric conversion device. The crystal may include different kinds of compounds. Exemplary compounds may include Bismuth germinate (BGO), barium fluoride (BaFl), gadolinium silicate (GSO), Lutetium orthosilicate (LSO), Lutetium Yttrium orthosilicate (LYSO), or the like, or any combination thereof. The light guide may be optically coupled to the crystal to provide a light path to the photoelectric conversion device. During a PET scan of the subject, incident γ rays may strike the crystal to produce small bursts of visible or invisible light (e.g., an optical signal). The visible or invisible light may be converted to an electric signal (e.g., an electric pulse signal) by the photoelectric conversion device. In some embodiments, the photoelectric conversion device may include a photomultiplier (PMT), a silicon photomultiplier (SiPM), an avalanche photodiode (APD), or the like, or any combination thereof.

The processing device 120 may process data and/or information obtained from the medical device 110, the storage device 130, and/or the terminal(s) 140. For example, the processing device 120 may obtain data associated with coincidence events related to intrinsic background radiations of a plurality of crystals of a PET device. As another example, the processing device 120 may determine a first TOF difference corresponding to a coincidence event based on first time information and second time information. As another example, the processing device 120 may determine a second TOF difference corresponding to a coincidence event based on locations of two crystals that detect the coincidence event. As still another example, the processing device 120 may correct a TOF state of a PET device based on a first TOF difference and a second TOF difference.

In some embodiments, the processing device 120 may be a single server or a server group. The server group may be centralized or distributed. In some embodiments, the processing device 120 may be local or remote. For example, the processing device 120 may access information and/or data from the medical device 110, the storage device 130, and/or the terminal(s) 140 via the network 150. As another example, the processing device 120 may be directly connected to the medical device 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be part of the terminal 140. In some embodiments, the processing device 120 may be part of the medical device 110.

The storage device 130 may store data, instructions, and/or any other information. In some embodiments, the storage device 130 may store data obtained from the medical device 110, the processing device 120, and/or the terminal(s) 140. The data may include image data acquired by the processing device 120, algorithms and/or models for processing the image data, etc. For example, the storage device 130 may store data associated with coincidence events related to intrinsic background radiations of a plurality of crystals of a PET device. As another example, the storage device 130 may store a first TOF difference and a second TOF difference corresponding to a coincidence event determined by the processing device 120. As still another example, the storage device 130 may store a reference energy spectrum determined by the processing device 120. In some embodiments, the storage device 130 may store data and/or instructions that the processing device 120 and/or the terminal 140 may execute or use to perform exemplary methods described in the present disclosure. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memories may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more other components in the medical system 100 (e.g., the processing device 120, the terminal(s) 140). One or more components in the medical system 100 may access the data or instructions stored in the storage device 130 via the network 150. In some embodiments, the storage device 130 may be integrated into the medical device 110.

The terminal(s) 140 may be connected to and/or communicate with the medical device 110, the processing device 120, and/or the storage device 130. In some embodiments, the terminal 140 may include a mobile device 141, a tablet computer 142, a laptop computer 143, or the like, or any combination thereof. For example, the mobile device 141 may include a mobile phone, a personal digital assistant (PDA), a gaming device, a navigation device, a point of sale (POS) device, a laptop, a tablet computer, a desktop, or the like, or any combination thereof. In some embodiments, the terminal 140 may include an input device, an output device, etc. The input device may include alphanumeric and other keys that may be input via a keyboard, a touchscreen (for example, with haptics or tactile feedback), a speech input, an eye tracking input, a brain monitoring system, or any other comparable input mechanism. Other types of the input device may include a cursor control device, such as a mouse, a trackball, or cursor direction keys, etc. The output device may include a display, a printer, or the like, or any combination thereof.

The network 150 may include any suitable network that can facilitate the exchange of information and/or data for the medical system 100. In some embodiments, one or more components of the medical system 100 (e.g., the medical device 110, the processing device 120, the storage device 130, the terminal(s) 140, etc.) may communicate information and/or data with one or more other components of the medical system 100 via the network 150. For example, the processing device 120 and/or the terminal 140 may obtain data associated with coincidence events related to intrinsic background radiations of a plurality of crystals of a PET device from the PET device via the network 150. As another example, the processing device 120 and/or the terminal 140 may obtain information stored in the storage device 130 via the network 150. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network (VPN), a satellite network, a telephone network, routers, hubs, witches, server computers, and/or any combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired and/or wireless network access points such as base stations and/or internet exchange points through which one or more components of the Medical system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. However, those variations and modifications do not depart the scope of the present disclosure. In some embodiments, the medical system 100 may include one or more additional components and/or one or more components of the medical system 100 described above may be omitted. Additionally or alternatively, two or more components of the medical system 100 may be integrated into a single component. A component of the medical system 100 may be implemented on two or more sub-components.

In some embodiments, a PET system may include a detector sub-system, an electronic system, a data correction sub-system, and/or a reconstruction sub-system. During a PET scan of a subject (e.g., a patient), after a PET tracer is introduced into the subject, the PET tracer molecules may emit positrons, namely the antiparticles of electrons. A positron has the same mass and the opposite electrical charge of an electron, and it undergoes an annihilation (also referred to as an "annihilation event" or a "coincidence event" or a "clinical coincidence event") with an electron (that may naturally exist in abundance within the subject) as the two particles collide. An electron-positron annihilation may result in two particles (e.g., two 511 keV γ photons), which, upon their own generation, begin to travel in opposite directions with respect to one another. In some embodiments, each of the γ photons may strike a crystal of the detector system to produce small bursts of visible or invisible light (e.g., an optical signal). The visible or invisible light may be converted to an electric signal by a photoelectric conversion device coupled to the crystal. The electric signal may be transmitted to a front-end circuit of the electronic system for waveform amplification and shaping, noise filtering, and/or discrimination logic selection. A processed electric signal may be transmitted to a back-end circuit of the electronic system for digital processing, to obtain position information, time information and/or energy information of the γ photons. The data correction system may correct the position information, time information and/or energy information of the γ photons to generate information of the coincidence event associated with the γ photons. The reconstruction system may generate a PET image based on the information of the coincidence event.

Figures 2, 3:
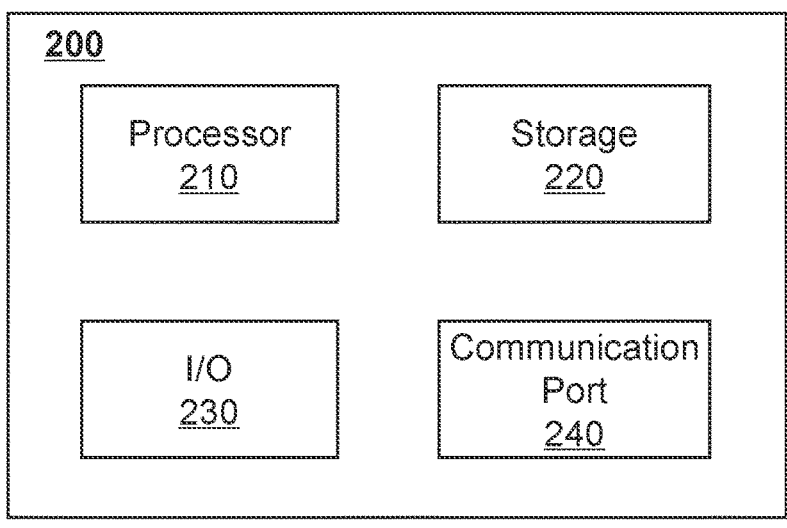
FIG. 2 is a schematic diagram illustrating exemplary hardware and/or software components of an exemplary computing device on which the processing device may be implemented according to some embodiments of the present disclosure.
FIG. 3 is a schematic diagram illustrating exemplary hardware and/or software components of an exemplary mobile device on which the terminal(s) may be implemented according to some embodiments of the present disclosure.

FIG. 2 is a schematic diagram illustrating exemplary hardware and/or software components of an exemplary computing device 200 on which the processing device 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process imaging data obtained from the medical device 110, the terminal(s) 140, the storage device 130, and/or any other component of the medical system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 200. However, it should be noted that the computing device 200 in the present disclosure may also include multiple processors. Thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the medical device 110, the terminal(s) 140, the storage device 130, and/or any other component of the Medical system 100. The storage 220 may be similar to the storage device 130 described in connection with FIG. 1, and the detailed descriptions are not repeated here.

The I/O 230 may input and/or output signals, data, information, etc. In some embodiments, the I/O 230 may enable a user interaction with the processing device 120. In some embodiments, the I/O 230 may include an input device and an output device. Examples of the input device may include a keyboard, a mouse, a touchscreen, a microphone, a sound recording device, or the like, or a combination thereof. Examples of the output device may include a display device, a loudspeaker, a printer, a projector, or the like, or a combination thereof. Examples of the display device may include a liquid crystal display (LCD), a light-emitting diode (LED)-based display, a flat panel display, a curved screen, a television device, a cathode ray tube (CRT), a touchscreen, or the like, or a combination thereof.

The communication port 240 may be connected to a network (e.g., the network 150) to facilitate data communications. The communication port 240 may establish connections between the processing device 120 and the medical device 110, the terminal(s) 140, and/or the storage device 130. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. In some embodiments, the communication port 240 may be and/or include a standardized communication port, such as RS232, RS485. In some embodiments, the communication port 240 may be a specially designed communication port. For example, the communication port 240 may be designed in accordance with the digital imaging and communications in medicine (DICOM) protocol.

FIG. 3 is a schematic diagram illustrating exemplary hardware and/or software components of an exemplary mobile device 300 according to some embodiments of the present disclosure. In some embodiments, the terminal(s) 140 and/or the processing device 120 may be implemented on the mobile device 300, respectively.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300.

In some embodiments, the communication platform 310 may be configured to establish a connection between the mobile device 300 and other components of the medical system 100, and enable data and/or signal to be transmitted between the mobile device 300 and other components of the medical system 100. For example, the communication platform 310 may establish a wireless connection between the mobile device 300 and the medical device 110, and/or the processing device 120. The wireless connection may include, for example, a Bluetooth™ link, a Wi-Fi™ link, a WiMax™ link, a WLAN link, a ZigBee link, a mobile network link (e.g., 3G, 4G, 5G), or the like, or any combination thereof. The communication platform 310 may also enable the data and/or signal between the mobile device 300 and other components of the medical system 100. For example, the communication platform 310 may transmit data and/or signals inputted by a user to other components of the medical system 100. The inputted data and/or signals may include a user instruction. As another example, the communication platform 310 may receive data and/or signals transmitted from the processing device 120. The received data and/or signals may include imaging data acquired by a detector of the medical device 110.

In some embodiments, a mobile operating system (OS) 370 (e.g., iOS™ Android™, Windows Phone™, etc.) and one or more applications (App(s)) 380 may be loaded into the memory 360 from the storage 390 in order to be executed by the CPU 340. The applications 380 may include a browser or any other suitable mobile apps for receiving and rendering information respect to motion signal recalibration or other information from the processing device 120. User interactions with the information stream may be achieved via the I/O 350 and provided to the processing device 120 and/or other components of the Medical system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 4:
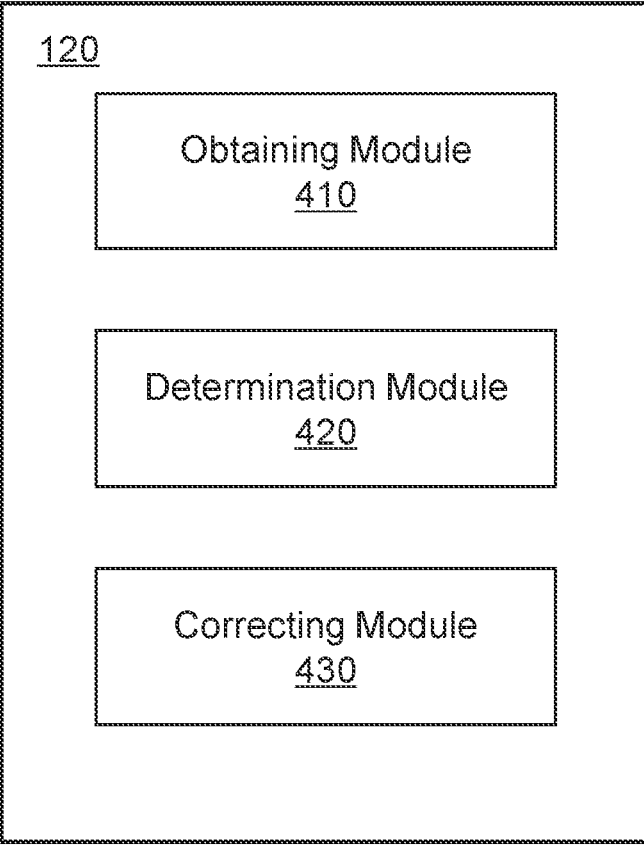
FIG. 4 is a schematic diagram illustrating an exemplary processing device according to some embodiments of the present disclosure.

FIG. 4 is a block diagram illustrating an exemplary processing device according to some embodiments of the present disclosure. In some embodiments, the processing device 120 may include an obtaining module 410, a determination module 420, and a correcting module 430.

The obtaining module 410 may be configured to obtain data and/or information associated with the medical system 100. The data and/or information associated with the medical system 100 may include data associated with coincidence events related to intrinsic background radiations of a plurality of crystals of a PET device, a first TOF difference corresponding to a coincidence event, a second TOF difference corresponding to a coincidence event, a reference energy spectrum, a reference peak position in a reference energy spectrum, a target peak position, or the like, or any combination thereof. For example, the obtaining module 410 may obtain data associated with a single event or a coincidence event related to an intrinsic background radiation of a crystal of the PET device. More descriptions of the data associated with a single event or a coincidence event related to an intrinsic background radiation of a crystal of the PET device may be found elsewhere in the present disclosure (e.g., FIG. 5 and descriptions thereof). In some embodiments, the obtaining module 410 may obtain the data and/or the information associated with the medical system 100 from one or more components (e.g., the medical device 110, the storage device 130, the terminal 140) of the medical system 100 via the network 150.

The determination module 420 may be configured to determine data and/or information associated with the medical system 100. For example, the determination module 420 may determine a first TOF difference corresponding to a coincidence event based on first time information and second time information. As another example, the determination module 420 may determine a second TOF difference corresponding to a coincidence event based on locations of two crystals that detect the coincidence event. More descriptions for determining a first TOF difference and a second TOF difference may be found elsewhere in the present disclosure (e.g., FIG. 5 and descriptions thereof). As still another example, the determination module 420 may generate a time spectrum of a crystal. As still another example, the determination module 420 may determine an offset value for a crystal based on a time spectrum. As still another example, the determination module 420 may determine whether an iterative operation satisfies a condition based on an offset value. As still another example, the determination module 420 may adjust a TOF state of a crystal based on an offset value for the crystal. As still another example, the determination module 420 may determine a TOF correction value for a crystal by summing one or more offset values for the crystal in one or more iterations. As still another example, the determination module 420 may generate a reference energy spectrum based on energy information of a single event or a coincidence event. As still another example, the determination module 420 may determine a reference peak position in a reference energy spectrum. As still another example, the determination module 420 may determine a target peak position based on a reference peak position in a reference energy spectrum. As still another example, the determination module 420 may determine an energy correction state based on a target peak position and a corrected peak position.

The correcting module 430 may be configured to correct data and/or information associated with the medical system 100. For example, the correcting module 430 may correct a TOF state of a PET device based on a first TOF difference and a second TOF difference. More descriptions for correcting a TOF state of a PET device may be found elsewhere in the present disclosure (e.g., FIGS. 5, 6, and descriptions thereof). As another example, the correcting module 430 may correct an energy state of a PET device based on an energy correction state. More descriptions for correcting an energy state of a PET device may be found elsewhere in the present disclosure (e.g., FIG. 7 and descriptions thereof).

It should be noted that the above description of the processing device 120 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more modules may be combined into a single module. For example, the determination module 420 and the correcting module 430 may be combined into a single module. In some embodiments, one or more modules may be added or omitted in the processing device 120. For example, the processing device 120 may further include a storage module (not shown in FIG. 4) configured to store data and/or information (e.g., data associated with a coincidence event, a first TOF difference corresponding to a coincidence event, a second TOF difference corresponding to a coincidence event, a reference energy spectrum, an energy correction state of a medical device) associated with the medical system 100.

FIG. 5 is a flowchart illustrating an exemplary process for correcting a TOF state of a PET device according to some embodiments of the present disclosure. In some embodiments, the process 500 may be implemented in the medical system 100 illustrated in FIG. 1. For example, the process 500 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 500 may be accomplished with one or more additional operations not described, and/or without one or more of the operations discussed. Additionally, the order in which the operations of the process 500 as illustrated in FIG. 5 and described below is not intended to be limiting.

In 510, the processing device 120 (e.g., the obtaining module 410) may obtain data associated with coincidence events related to intrinsic background radiations of a plurality of crystals of a PET device. Each of the coincidence events may be detected by two crystals of the plurality of crystals of the PET device. The data associated with the each coincidence event may include first time information and/or second time information.

In some embodiments, the PET device may include a plurality of detectors. The plurality of detectors may be arranged in the form of a ring, a cylinder, a portion thereof, to surround a subject to be scanned. In some embodiments, the detector may include a crystal (e.g., a scintillator). In some embodiments, the crystal may emit a certain amount of radiation (also referred to as the intrinsic background radiation). For example, a Lutetium (Lu) based crystal (e.g., Lutetium orthosilicate (LSO), Lutetium Yttrium orthosilicate (LYSO)) may include radioactive isotopes of lutetium ($^{176}$Lu). The $^{176}$Lu may release one or more β particles (with an energy range from 0 keV to 593 keV) and one or more γ particles (with an energy of 88, 202, or 307 keV) when it decays.

In some embodiments, the β particle emitted from a first crystal (e.g., the Lutetium based crystal) may deposit energies in the first crystal, and may only be detected by the first crystal. The γ particles emitted from the first crystal may not only detected by the first crystal, but also by a second crystal after emitting outside the first crystal. In some embodiments, a single event may include a β event and a γ event. The β event may refer to an event that the β particle emitted from the first crystal is detected by the first crystal. The γ event may refer to an event that the γ particle emitted from the first crystal is detected by the second crystal. In some embodiments, if the γ particle and the β particle are received and interact with two crystals within a certain time window (e.g., 1 nanosecond, 2 nanoseconds, 5 nanoseconds, 10 nanoseconds, 20 nanoseconds), it may be determined that the two particles come from a same intrinsic background radiation, and accordingly, the γ event and the β event may be regarded as a coincidence event.

In some embodiments, the data associated with the coincidence event related to the intrinsic background radiation of the crystal may include time information, energy information, or the like, or any combination thereof. The time information may include the first time information and/or the second time information. The first time information may correspond to the β event. The second time information may correspond to the γ event. The first time information may include a time when the β particle is detected by the first crystal (also referred to as a detection time of the β particle). The second time information may include a time when the γ particle is detected by the second crystal (also referred to as a detection time of the γ particle).

In some embodiments, the processing device 120 may obtain a first optical signal excited by the β particle and a second optical signal excited by the γ particle. The processing device 120 may obtain a first electric signal by converting the first optical signal. The processing device 120 may obtain a second electric signal by converting the second optical signal. For example, the β particle (and/or the γ particle) may strike the corresponding crystal to produce small bursts of visible or invisible light (i.e., the first optical signal, the second optical signal). The first optical signal (and/or the second optical signal) may be converted to the first electric signal (and/or the second electric signal) by a photoelectric conversion device coupled to the corresponding crystal, respectively. The processing device 120 may determine the first time information based on the first electric signal. The processing device 120 may determine the second time information based on the second electric signal. For example, the processing device 120 may determine a time when the first electric signal is generated as the detection time of the β particle. The processing device 120 may determine a time when the second electric signal is generated as the detection time of the γ particle.

Figure 8:
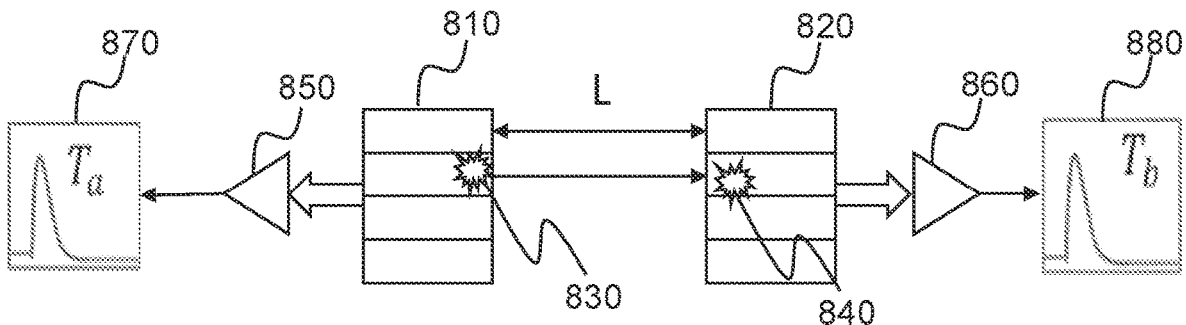
FIG. 8 illustrates an exemplary intrinsic background radiation of a crystal of a PET device according to some embodiments of the present disclosure.

FIG. 8 illustrates an exemplary intrinsic background radiation of a crystal of a PET device according to some embodiments of the present disclosure. As shown in FIG. 8, a PET device may include a first crystal 810 and a second crystal 820. The first crystal 810 may release a β particle 830 and at least one γ particle 840 when it decays. The β particle 830 may strike the first crystal 810 to generate a first optical signal (also referred to as a β event). The γ particle 840 may emit out of the first crystal 810 and may strike the second crystal 820 to generate a second optical signal (also referred to as a γ event). The first optical signal may be converted to a first electric signal by a first photoelectric conversion device 850 coupled to the first crystal 810. The second optical signal may be converted to a second electric signal by a second photoelectric conversion device 860 coupled to the second crystal 820. First time information 870 corresponding to the β event may be generated or obtained based on the first electric signal. Second time information 880 corresponding to the γ event may be generated or obtained based on the second electric signal.

In some embodiments, a first detector including the first crystal and a second detector including the second crystal may be spaced apart from each other. In some embodiments, the PET device may include a plurality of detectors (e.g., a first detector, a second detector, a third detector, a fourth detector, a fifth detector, a sixth detector, a seventh detector, an eighth detector). The plurality of detectors may be arranged in the form of a ring. For example, the first detector may be adjacent to the second detector, the second detector may be adjacent to the third detector, the third detector may be adjacent to the fourth detector, the fourth detector may be adjacent to the fifth detector, the fifth detector may be adjacent to the sixth detector, the sixth detector may be adjacent to the seventh detector, the seventh detector may be adjacent to the eighth detector, the eighth detector may be adjacent to the first detector. In some embodiments, in the intrinsic background radiation of a crystal of the first detector, a γ particle emitted from the crystal of the first detector may be detected by the third detector, the fourth detector, the fifth detector, the sixth detector, the seventh detector, and cannot be detected by the second detector or the eighth detector adjacent to the first detector. It should be noted that the PET device may include any number of detectors, and the plurality of detectors may be arranged in any suitable manner. Accordingly, since the two crystals that detect the coincidence event are spaced apart from each other, the distance between the two crystals may be relatively long, and the TOF of the γ particle between the two crystals may be relatively long. Due to a relatively small order of magnitude of parameters associated with the coincidental event, by increasing the distance between the two crystals that detect the coincidence event, the calculation difficulty of the parameters associated with the coincidental event may be reduced and the calculation accuracy of the parameters associated with the coincidental event may be improved.

In some embodiments, the processing device 120 may obtain the data associated with the coincidence events based on a target energy window and a target time window. In some embodiments, the target energy window may be determined based on a β particle energy (e.g., 0 keV~593 keV), a γ particle energy (e.g., 88 keV, 202 keV, 307 keV), a reference energy, or the like, or any combination thereof. In some embodiments, the reference energy may be a clinical energy (e.g., 511 keV). In some embodiments, the target energy window may be larger than the β particle energy, the γ particle energy, and/or the clinical energy. For example, the target energy window may be in a range from 200 keV to 650 keV.

In some embodiments, the target time window may be determined based on a reference time window (e.g., a clinical time window). For example, the target time window may be larger than the clinical time window. During a PET scan of a subject (e.g., a patient), the subject may usually be located in the center of a field of view (FOV) of the PET device, and an annihilation location where two 511 keV γ photons are generated in a clinical coincidence event may be in the body of the subject. An annihilation location where two particles (e.g., the β particle, the γ particle) are generated in the coincidence event related to the intrinsic background radiation of the crystal of the PET device may be in the crystal. That is, a travel distance of the γ particle generated in the coincidence event related to the intrinsic background radiation may be longer than a travel distance of the γ particle generated in the clinical coincidence event. Accordingly, the time of the γ particle travels from the first crystal to the second crystal in the coincidence event related to the intrinsic background radiation may be longer than the time of the γ particle travels from the annihilation location to a corresponding detector of the PET device in the clinical coincidence event. Therefore, the target time window may be larger than the clinical time window, such that the PET device can obtain the data associated with the coincidence event related to the intrinsic background radiation of the crystal of the PET device.

In 520, the processing device 120 (e.g., the determination module 420) may determine a first time of fight (TOF) difference corresponding to the each coincidence event based on the first time information and the second time information.

In some embodiments, the first TOF difference may be a measured time difference between two detection times of two particles generated in the coincidence event. For example, the first TOF difference may be a time difference between a detection time of the β particle (or the detection time of the γ particle) and a detection time of the γ particle (or the detection time of the β particle).

In some embodiments, the processing device 120 may determine the first TOF difference corresponding to the coincidence event based on the first time information and the second time information corresponding to the coincidence event. For example, the processing device 120 may determine a time difference between the first time information and the second time information as the first TOF difference.

In some embodiments, the processing device 120 may correct the first TOF difference based on one or more correction algorithms. For example, the processing device 120 may perform a time walk effect correction on the first TOF difference. In the PET device, a time readout circuit may be used to obtain an arrival time of a leading edge of an input signal. The time readout circuit may amplify the input signal, and then discriminate the arrival time of the leading edge of the signal by a leading edge discriminator (LED), thereby determining the time information of the signal. However, amplitudes of different input signals may be different. The leading edge of a signal with a relatively small amplitude may arrive at the leading edge discriminator later than the leading edge of a signal with a relatively large amplitude, and a time walk effect may be generated, which may lead to the inaccurate timing of the time readout circuit. Therefore, the time walk effect correction may be performed on the first TOF difference to reduce the time walk effect. As another example, the processing device 120 may perform a position correction on the first TOF difference. The position correction may be used to correct a difference in time walk effect due to different locations of detectors of the PET device. Accordingly, by correcting the first TOF difference based on the one or more correction algorithms, the accuracy of the first TOF difference may be improved.

In 530, the processing device 120 (e.g., the determination module 420) may determine a second TOF difference corresponding to the each coincidence event based on locations of the two crystals that detect the each coincidence event.

In some embodiments, the second TOF difference may be an actual time difference between two detection times of two particles generated in the coincidence event. For example, the second TOF difference may be a time for the γ particle to escape from the first crystal to second crystal.

In some embodiments, the processing device 120 may determine the second TOF difference based on a distance between the location of the first crystal and the location of the second crystal and a speed of the γ particle (i.e., a speed of light). For example, the processing device 120 may determine the second TOF difference by dividing the distance between the location of the first crystal and the location of the second crystal by the speed of light.

In 540, the processing device 120 (e.g., the correcting module 430) may correct the PET device (e.g., a TOF state of the PET device) based on the first TOF difference and the second TOF difference.

As used herein, a TOF state of a PET device refers to TOF information of coincidence events detected by one or more crystals of the PET device. In some embodiments, the processing device 120 may determine whether a TOF state of each crystal of the plurality of crystals of the PET device needs to be corrected based on the first TOF difference and the second TOF difference corresponding to at least one coincidence event detected between the each crystal and other crystals. In some embodiments, if at least one component (e.g., a photoelectric conversion device, a back-end circuit) of the PET device is malfunctioning, the first time information and the second time information may be inaccurate, and the first TOF difference determined based on the first time information and the second time information may also be inaccurate. That is, the first TOF difference measured by the PET device may be different from the second TOF difference.

In some embodiments, for a specific crystal of the plurality of crystals of the PET device, the processing device 120 may determine a TOF correction value for the specific crystal. For example, the processing device 120 may determine a difference value (i.e., the TOF correction value) between the first TOF difference and the second TOF difference corresponding to a coincidence event detected between the specific crystal and another crystal. The processing device 120 may determine whether the difference value is less than a first difference threshold. In response to determining that the difference value is less than the first difference threshold, the processing device 120 may determine that the TOF state of the specific crystal does not need to be corrected. In response to determining that the difference value is not less than the first difference threshold, the processing device 120 may determine that the TOF state of the specific crystal needs to be corrected.

In some embodiments, for a specific crystal of a plurality of crystals of the PET device, the processing device 120 determine a plurality of pairs of first TOF difference and second TOF difference corresponding to each of a plurality of coincidence events detected between the specific crystal and other crystals. The processing device 120 may determine a difference value between the first TOF difference and the second TOF difference in each of the plurality of pairs of first TOF difference and second TOF difference. The processing device 120 may determine an average value (i.e., the TOF correction value) of a plurality of difference values corresponding to the plurality of pairs of first TOF difference and second TOF difference. The processing device 120 may determine whether the average value is less than a second difference threshold. In response to determining that the average value is less than the second difference threshold, the processing device 120 may determine that the TOF state of the specific crystal does not need to be corrected. In response to determining that the average value is not less than the second difference threshold, the processing device 120 may determine that the TOF state of the specific crystal needs to be corrected.

In some embodiments, for a specific crystal of the plurality of crystals of the PET device, the processing device 120 may generate a time spectrum based on the first TOF difference and the second TOF difference corresponding to each of one or more of the coincidence events detected between the specific crystal and other crystals. The processing device 120 may determine the TOF correction value based on the time spectrum. For example, the processing device 120 may determine the TOF correction value based on the time spectrum according to an iterative operation including one or more iterations. More descriptions for determining the TOF correction value based on the time spectrum may be found elsewhere in the present disclosure (e.g., FIG. 6 and descriptions thereof).

The processing device 120 may correct the TOF state of the PET device based on the TOF correction value corresponding to each crystal of the plurality of crystals of the PET device. In some embodiments, the processing device 120 may record one or more TOF correction values corresponding to one or more crystals of the plurality of crystals of the PET device in a correction file of the PET device (also referred to as an offline correction mode). During a scan of a subject (e.g., a patient), the processing device 120 may correct TOF information of one or more coincidence events that is detected by the one or more crystals based on the one or more TOF correction values corresponding to one or more crystals in the correction file of the PET device. For example, if a TOF correction value corresponding to a specific crystal is +50 time unit, a target detection time of a particle generated in a coincidence event that is detected by the specific crystal may be determined by subtracting 50 time unit from an original detection time of the particle. Accordingly, by recording the TOF correction value in the correction file of the PET device, the TOF state of the PET device may be corrected offline, the correction process may be simple, the correction time may be reduced, and the efficiency of the correction process may be improved.

In some embodiments, the processing device 120 may program the one or more TOF correction values corresponding to the one or more crystals of the plurality of crystals of the PET device in one or more detectors of the PET device (also referred to as an online correction mode). For example, the processing device 120 may program the one or more TOF correction values in front-end circuits of the one or more detectors of the PET device. Accordingly, by programming the one or more TOF correction values in the front-end circuits of the one or more detectors of the PET device, the TOF state of the PET device may be corrected online, and the correction effect may be improved.

In some embodiments, the correction mode (e.g., the offline correction mode, the online correction mode) may be determined based on actual needs and/or the TOF correction value. For example, if an absolute value of the TOF correction value is relatively large (e.g., larger than a threshold), the TOF state of the PET device may be corrected according to the online correction mode. If the absolute value of the TOF correction value is relatively small (e.g., smaller than a threshold), the TOF state of the PET device may be corrected according to the offline correction mode.

In some embodiments, a deviation of the TOF state of the PET device may be caused by the malfunctioning of any component of the PET device. The position of the malfunctioning component cannot be determined only based on the TOF correction value, and accordingly the TOF state of the PET device cannot be corrected by repairing the malfunctioning component. Therefore, by recording the TOF correction value in the correction file of the PET device or programming the TOF correction value in the one or more detectors of the PET device, the TOF state of the PET device may be corrected without determining the malfunctioning reason of the PET device and repairing the malfunctioning component of the PET device, which may improve the accuracy and efficiency of the correction process.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, process 500 may include an operation for correcting an energy state of the PET device based on the data associated with the coincidence events. More descriptions for correcting the energy state of the PET device may be found elsewhere in the present disclosure (e.g., FIG. 7 and descriptions thereof). In some embodiments, during the correction process of the PET device, in order to prevent a subject located in the FOV of the PET device from absorbing γ rays emitted from the intrinsic background radiations of the plurality of crystals of the PET device, no subject may be placed in the FOV of the PET device.

FIG. 6 is a flowchart illustrating an exemplary process for determining a TOF correction value according to some embodiments of the present disclosure. In some embodiments, the process 600 may be implemented in the medical system 100 illustrated in FIG. 1. For example, the process 600 may be stored in the storage device 130 and/or storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 610, for each crystal of a plurality of crystals of a PET device, the processing device 120 (e.g., the determination module 420) may generate a time spectrum of the crystal.

In some embodiments, for a first iteration in the iterative operation, the processing device 120 may generate the time spectrum based on a first TOF difference and a second TOF difference corresponding to each of one or more coincidence events detected between the crystal and other crystals of a PET device. In some embodiments, the time spectrum may satisfy the Gaussian distribution. For example, for each of the one or more (e.g., all) coincidence events detected between the crystal and other crystals, the processing device 120 may determine a time difference between the first TOF difference and the second TOF difference corresponding to the coincidence event. The processing device 120 may generate the time spectrum of the crystal based on one or more time differences corresponding to the one or more coincidence events detected between the crystal and other crystals.

In some embodiments, a time spectrum of a specific crystal may reflect a relationship between a count of coincidence events and a time difference between a first TOF difference and a second TOF difference corresponding to each of a plurality of coincidence events detected between the specific crystal and other crystals. For example, the horizontal axis of the time spectrum may refer to Tbin. The Tbin may be determined based on a time difference between a first TOF difference and a second TOF difference corresponding to a coincidence event, and a time unit. For example, the Tbin may be determined by dividing the time difference by the time unit. The time unit may be manually set by a user of the medical system 100, or be determined by one or more components (e.g., the processing device 120) of the medical system 100. For example, the time unit may be 10, 20, 30, or the like. The vertical axis of the time spectrum may refer to a count of coincidence events. In some embodiments, it is assumed that TOF states of the other crystals are normal, the processing device 120 may generate the time spectrum of the specific crystal by accumulating a plurality of time differences corresponding to the plurality of coincidence events detected between the specific crystal and other crystals. For example, for each of the plurality of coincidence events detected between the specific crystal and other crystals, the processing device 120 may determine a time difference between a first TOF difference and a second TOF difference corresponding to the coincidence event. The processing device 120 may determine which Tbin the time difference belongs to, and add 1 to the cumulative count of coincidence events corresponding to the Tbin.

In 620, the processing device 120 (e.g., the determination module 420) may determine an offset value for the crystal based on the time spectrum.

In some embodiments, the processing device 120 may determine the offset value for the crystal based on an expected value of the time spectrum with the Gaussian distribution. For example, the processing device 120 may determine the expected value of the time spectrum with the Gaussian distribution as the offset value for the crystal in a current iteration. In some embodiments, if the TOF state of the crystal (also referred to as TOF information of the crystal in the present disclosure) is normal, the expected value of the time spectrum with the Gaussian distribution for the crystal may be zero, and the offset value may also be zero. If the TOF state of the crystal is abnormal, the expected value of the time spectrum with the Gaussian distribution may be less than or greater than zero, and offset value may be the expected value. As used herein, a TOF state of a crystal refers to TOF information of coincidence events detected by the crystal.

In 630, the processing device 120 (e.g., the determination module 420) may determine whether an iterative operation satisfies a condition based on the offset value.

In some embodiments, the processing device 120 may determine whether the iterative operation satisfies the condition based on offset values for the plurality of crystals of the PET device. For example, the condition may be satisfied if the offset value for each crystal of the plurality of crystals is smaller than a threshold. As another example, the termination condition may be satisfied if the variation of offset values for each crystal of the plurality of crystals in two or more consecutive iterations is smaller than a threshold.

In 640, in response to determining that the iterative operation does not satisfy the condition, the processing device 120 (e.g., the determination module 420) may adjust a TOF state of the crystal based on the offset value for the crystal.

In some embodiments, for each crystal of the plurality of crystals of the PET device, the processing device 120 may adjust the TOF state of the crystal based on the offset value for the crystal, such that a time spectrum of the adjusted crystal does not shift. As used herein, an adjusted crystal refers to a crystal whose TOF state is adjusted based on the offset value for the crystal. That is, the offset value of the time spectrum of the adjusted crystal may be zero.

In some embodiments, the processing device 120 may adjust the TOF state of the crystal by adjusting data associated with coincidence events that is detected by the crystal. For example, the processing device 120 may adjust time information (e.g., the first time information, the second time information) of the coincidence events that is detected by the crystal. Merely by way of example, if an offset value for a crystal in a current iteration is +50 time units, a target detection time of a particle generated in a coincidence event that is detected by the crystal may be determined by subtracting 50 time unit from an original detection time of the particle. The first TOF difference may be adjusted based on a corrected first time information and/or a corrected second time information.

Figure 9:
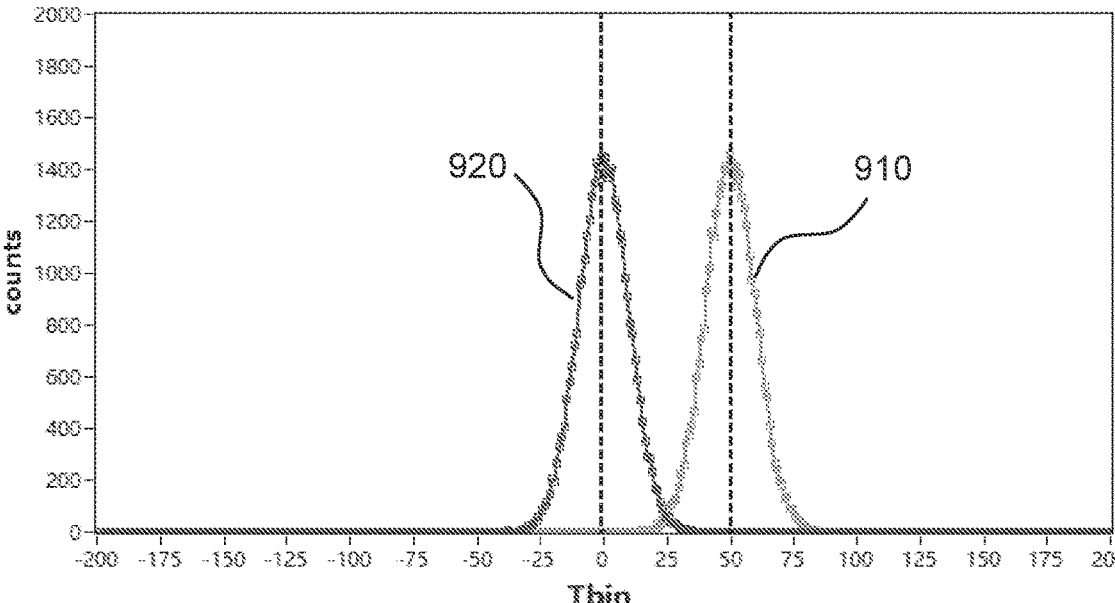
FIG. 9 illustrates an exemplary time spectrum according to some embodiments of the present disclosure.

FIG. 9 illustrates an exemplary time spectrum of a crystal according to some embodiments of the present disclosure. The horizontal axis of a time spectrum may refer to Tbin. The vertical axis of the time spectrum may refer to a count of radiation events (e.g., coincidence events). As shown in FIG. 9, a time spectrum 910 of a crystal satisfies the Gaussian distribution. An expected value of the time spectrum 910 is +50 time units. An offset value for the crystal may be determined as +50 time units. After the TOF state of the crystal is corrected, a time spectrum 920 of the crystal is generated. An expected value of the time spectrum 920 is 0 time unit.

In some embodiments, operations 610-630 may be repeated until the iterative operation satisfies the condition. For example, in a next iteration, for each crystal of the plurality of crystals of the PET device, the processing device 120 may generate a time spectrum of the crystal based on adjusted data associated with coincidence events (e.g., the adjusted first time information, the adjusted second time information) detected between the crystal and other crystals as described in connection with operation 610. The processing device 120 may determine an offset value for the crystal based on the time spectrum as described in connection with operation 620. The processing device 120 may determine whether the iterative operation satisfies the condition based on the offset value for the crystal as described in connection with operation 630.

In some embodiments, in each iteration of the one or more iterations of the iterative operation, a same set of data associated with the coincidence events related to the intrinsic background radiations of the plurality of crystals of the PET device may be used. In some embodiments, in different iterations of the iterative operation, different sets of data associated with the coincidence events related to the intrinsic background radiations of the plurality of crystals of the PET device may be used. For example, in a first iteration of the iterative operation, the processing device 120 may obtain a first set of data associated with the coincidence events related to the intrinsic background radiations of the plurality of crystals of the PET device. In a second iteration of the iterative operation, the processing device 120 may obtain a second set of data associated with the coincidence events related to the intrinsic background radiations of the plurality of crystals of the PET device. The first set of data and the second set of data may be associated with different coincidence events related to the intrinsic background radiations of the plurality of crystals of the PET device.

In 650, in response to determining that the iterative operation satisfies the condition, the processing device 120 (e.g., the determination module 420) may determine a TOF correction value for the crystal by summing one or more offset values for the crystal in one or more iterations.

In some embodiments, the processing device 120 may determine the TOF correction value for a specific crystal by summing one or more offset values for the specific crystal in the one or more iterations. For example, the processing device 120 may determine a sum of the one or more offset values for the specific crystal in the one or more iterations as the TOF correction value for the specific crystal. As another example, the processing device 120 may determine an additive inverse of the sum of the one or more offset values for the specific crystal in the one or more iterations as the TOF correction value for the specific crystal. Further, the processing device 120 may correct a TOF state of the PET device based on the TOF correction value for each of the plurality of crystals of the PET device as described in connection with operation 540.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 7:
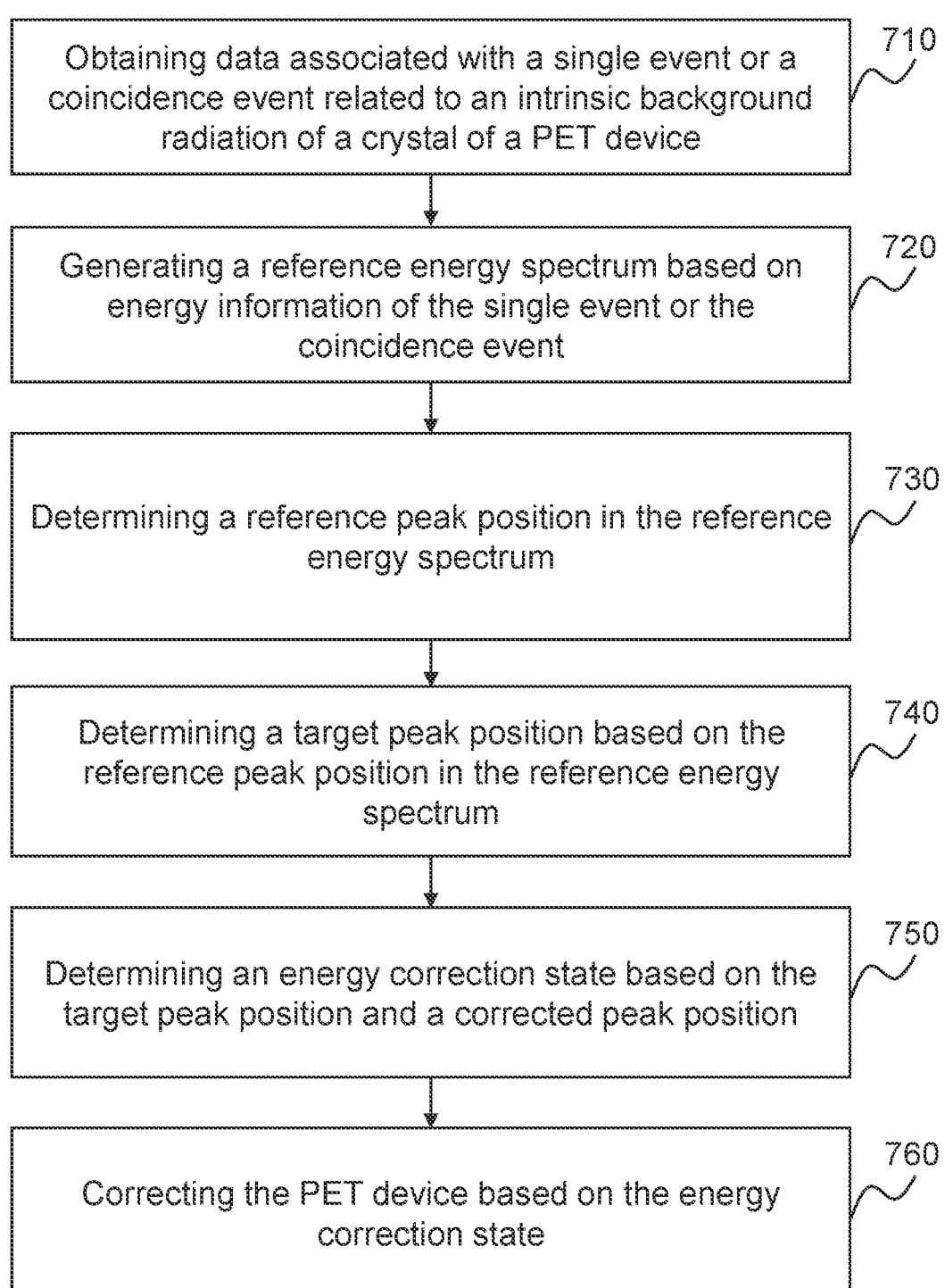
FIG. 7 is a flowchart illustrating an exemplary process for correcting a PET device according to some embodiments of the present disclosure.

FIG. 7 is a flowchart illustrating an exemplary process for correcting an energy state of a PET device according to some embodiments of the present disclosure. In some embodiments, the process 700 may be implemented in the medical system 100 illustrated in FIG. 1. For example, the process 700 may be stored in the storage device 130 and/or the storage (e.g., the storage 220, the storage 390) as a form of instructions, and invoked and/or executed by the processing device 120 (e.g., the processor 210 of the computing device 200 as illustrated in FIG. 2, the CPU 340 of the mobile device 300 as illustrated in FIG. 3). The operations of the illustrated process presented below are intended to be illustrative. In some embodiments, the process 700 may be accomplished with one or more additional operations not described, and/or without one or more of the operations discussed. Additionally, the order in which the operations of the process 700 as illustrated in FIG. 7 and described below is not intended to be limiting.

In 710, the processing device 120 (e.g., the obtaining module 410) may obtain data associated with a single event or a coincidence event related to an intrinsic background radiation of a crystal of the PET device.

Operation 710 may be performed in a similar manner as operation 510 as described in connection with FIG. 5, the descriptions of which are not repeated here.

In 720, the processing device 120 (e.g., the determination module 420) may generate a reference energy spectrum based on energy information of the single event or the coincidence event.

In some embodiments, the processing device 120 may generate the reference energy spectrum based on the energy information of the single event. In some embodiments, the processing device 120 may generate the reference energy spectrum based on time information and energy information of the coincidence event. For example, the coincidence event may include a β event and a γ event. The processing device 120 may generate the reference energy spectrum corresponding to the β event and/or the reference energy spectrum corresponding to the γ event based on time information of the β event and time information of the γ event. For example, the detection time of the γ event may be latter than the detection time of the β event. The processing device 120 may obtain the energy information of the β event and/or the energy information of the γ event based on the detection time of the γ event and the detection time of the β event. The processing device 120 may generate the reference energy spectrum corresponding to the β event and/or the reference energy spectrum corresponding to the γ event based on the energy information of β event and/or the energy information of γ event.

In some embodiments, the intrinsic background radiation generated from a Lu-based crystal may generate three types of γ particles with energy peaks of 307 keV, 202 keV, and 88 keV when decaying. The γ particles may strike a crystal of the PET device to produce an optical signal. The optical signal may be converted to an electric signal by a photoelectric conversion device (e.g., a PMT) coupled to the crystal. The electric signal may contain information regarding the energy peaks of the γ particles (i.e., the energy information of the γ event). The processing device 120 may generate the reference energy spectrum corresponding to the γ event by processing the electric signal. In some embodiments, the reference energy spectrum may have one or more peaks each of which corresponds to an energy. For example, the reference energy spectrum corresponding to the γ event may have a peak corresponding to 307 keV, a peak corresponding to 202 keV, and a peak corresponding to 88 keV.

In 730, the processing device 120 (e.g., the determination module 420) may determine a reference peak position in the reference energy spectrum.

Figure 10:
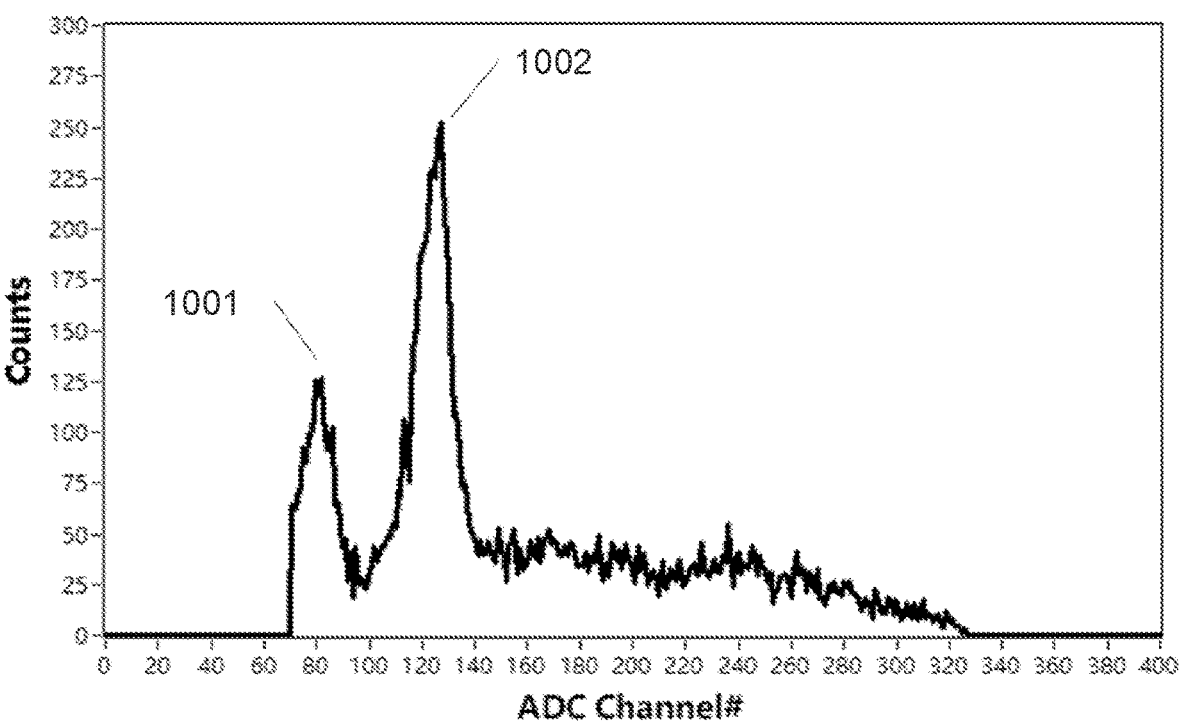
FIG. 10 illustrates an exemplary reference energy spectrum according to some embodiments of the present disclosure.

In some embodiments, the processing device 120 may identify one or more positions of one or more reference peaks (also referred to as one or more reference peak positions) in the reference energy spectrum. FIG. 10 illustrates an exemplary reference energy spectrum according to some embodiments of the present disclosure. The radiation source is the intrinsic background radiation generated by a Lu-based crystal. The horizontal axis of a reference energy spectrum 1000 may refer to an analog-to-digital converter (ADC) channel value. The vertical axis of the reference energy spectrum 1000 may refer to a PET count (e.g., a count of radiation events). The ADC channel value may be a sampled value of the ADC. The ADC channel value may reflect energy information of the radiation events. As shown in FIG. 10, a reference peak position 1001 corresponding to 202 keV and a reference peak position 1002 corresponding to 307 keV are determined in the reference energy spectrum 1000.

In 740, the processing device 120 (e.g., the determination module 420) may determine a target peak position based on the reference peak position in the reference energy spectrum.

In some embodiments, the target peak position may be a measured peak position corresponding to a target energy in the reference energy spectrum. In some embodiments, the target energy may be an energy of a particle (e.g., a γ photon) emitted from an object with a PET radioactive tracer (e.g., $^{18}$F-fluorodeoxyglucose (FDG). For example, the target energy may be 511 keV.

In some embodiments, the processing device 120 may determine the target peak position based on the reference peak position and a relationship between a position of a peak (e.g., an ADC channel value) and an energy of the peak. For example, if the reference peak position corresponding to 307 keV (or 88 keV, 202 keV) is determined in the reference energy spectrum, the processing device 120 may determine the target peak position corresponding to 511 keV based on a relationship between a peak position corresponding to 307 keV (or 88 keV, 202 keV) and a peak position corresponding to 511 keV.

In some embodiments, the relationship between the position of the peak and the energy of the peak may be represented in the form of a table or curve recording different energies of the peak and their corresponding peak positions, a drawing, a mathematical expression, etc. In some embodiments, the relationship between the position of the peak and the energy of the peak may be determined based on a plurality of peak positions corresponding to particles of different energies generated by a plurality of radioactive sources (e.g., technetium-99 (Tc-99), fluorine-18 (F-18), indium-111 (In-111), iodine-131 (I-131)). In some embodiments, the processing device 120 may obtain a first peak position corresponding to a first particle with a first energy generated by a first radioactive source (also referred to as the first peak position corresponding to the first energy), a second peak position corresponding to a second particle with a second energy generated by a second radioactive source, a third peak position corresponding to a third particle with a third energy generated by a third radioactive source. The first energy, the second energy, and the third energy may be different. The first radioactive source, the second radioactive source, and the third radioactive source may be the same or different. The processing device 120 may determine the relationship between the position of the peak and the energy of the peak based on the first peak position, the second peak position, the third peak position, the first energy, the second energy, and the third energy. For example, the processing device 120 may generate a curve by fitting the first peak position corresponding to first energy, the second peak position corresponding to second energy, and the third peak position corresponding to the third energy. The processing device 120 may designate the curve as the relationship between the position of the peak and the energy of the peak.

In some embodiments, the relationship between the position of the peak and the energy of the peak may be stored in a storage device (e.g., the storage device 130) of the medical system 100. The processing device 120 may obtain the relationship between the position of the peak and the energy of the peak from the storage device (e.g., the storage device 130) of the medical system 100 when correcting the energy state of the PET device. In some embodiments, different crystals may correspond to different relationships between the position of the peak and the energy of the peak. In some embodiments, different crystals may correspond to a same relationship between the position of the peak and the energy of the peak.

In 750, the processing device 120 (e.g., the determination module 420) may determine an energy correction state based on the target peak position and a corrected peak position.

In some embodiments, the energy correction state of the PET device may indicate whether a peak position corresponding to an energy in an energy spectrum has shifted. In some embodiments, the corrected peak position may be an actual peak position corresponding to the target energy (e.g., 511 keV) in a target energy spectrum. In some embodiments, the processing device 120 may obtain data associated with a single event or a coincidence event associated with the 511 keV γ photons generated from a radioactive source such as $^{18}$F-fluorodeoxyglucose (FDG) or germanium-68 (Ge-68). The processing device 120 may generate the target energy spectrum based on energy information of the single event or the coincidence event corresponding to 511 keV γ photons. The processing device 120 may determine the corrected peak position in the target energy spectrum.

In some embodiments, the processing device 120 may determine the energy correction state by comparing the target peak position and the corrected peak position. For example, the processing device 120 may determine whether an offset between the target peak position and the corrected peak position is greater than an offset threshold. In response to determining that the offset between the target peak position and the corrected peak position is greater than the offset threshold, the processing device 120 may determine that the energy correction state is abnormal, and the energy state of the PET device needs to be corrected. As another example, the processing device 120 may determine whether a ratio between the target peak position and the corrected peak position is greater than a ratio threshold. In response to determining that the ratio between the target peak position and the corrected peak position is greater than the ratio threshold, the processing device 120 may determine that the energy correction state is abnormal, and the energy state of the PET device needs to be corrected. In some embodiments, the offset threshold and/or the ratio threshold may be determined manually by a user (e.g., a doctor) of the medical system 100, or by one or more components (e.g., the processing device 120) of the medical system 100 according to different situations.

In 760, the processing device 120 (e.g., the correcting module 430) may correct the PET device (e.g., an energy state of the PET device) based on the energy correction state.

In some embodiments, the processing device 120 may determine whether the energy state of the PET device needs to be corrected based on the energy correction state. In response to determining that the energy state of the PET device needs to be corrected, the processing device 120 may program the target peak position in one or more detectors of the PET device. For example, the processing device 120 may program the target peak position in front-end circuits of the one or more detectors of the PET device.

In some embodiments, the processing device 120 may correct a relationship between peak position and peak energy based on the energy correction state. For example, the processing device 120 may correct the peak position (e.g., the ADC channel value) of 511 keV γ photons based on the energy correction state. For example, the processing device 120 may designate the peak position of 511 keV γ photons as the target peak position.

In some embodiments, the processing device 120 may determine an energy window of a PET detector based on the energy correction state. As used herein, an energy window of a PET detector refers to an energy range of particles detected by the PET detector. In some embodiments, the energy window of the PET detector may be determined based on energies corresponding to one or more peaks of an energy spectrum of the radioactive tracer. For example, the energy window may include energies within an energy threshold range around the energy of a peak. For example, if an energy corresponding to a peak is 511 keV, and the energy threshold range is 100 keV, then the energy window may be determined as [411 keV, 611 keV]. In some embodiments, if a measured energy corresponding to γ photons is shifted from 511 keV to 400 keV, the energy window may be modified from [411 keV, 611 keV] to [300 keV, 500 keV]. Accordingly, by modifying the energy window based on the energy correction state, the accuracy of the acquisition of PET data (e.g., data associated with coincidence events) may be improved.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, for each crystal of a plurality of crystals of the PET device, process 700 may be performed to determine an energy correction state for the crystal. The energy state of the PET device may be corrected based on energy correction states for the plurality of crystals of the PET device.

In some embodiments, after the energy state of the PET device is corrected, the processing device 120 may obtain target data associated with a single event or a coincidence event related to an intrinsic background radiation of a crystal (e.g., a Lu-based crystal) of the PET device. The processing device 120 may generate a candidate energy spectrum based on energy information of the single event or the coincidence event. The processing device 120 may determine a candidate peak position in the candidate energy spectrum. During the energy state correction process (e.g., process 700) of the PET device, the processing device 120 may determine the energy correction state based on the candidate peak position and the reference peak position. In some embodiments, the processing device 120 may determine the energy correction state by comparing the candidate peak position and the reference peak position. For example, the processing device 120 may determine whether an offset between the candidate peak position and the reference peak position is greater than an offset threshold. In response to determining that the offset between the candidate peak position and the reference peak position is greater than the offset threshold, the processing device 120 may determine that the energy correction state is abnormal, and the energy state of the crystal of the PET device needs to be corrected.

In some embodiments, the processing device 120 may determine the energy correction state based on a plurality of candidate peak positions and a plurality of reference peak positions. For example, the processing device 120 may determine a first candidate peak position corresponding to 202 keV, and a second candidate peak position corresponding to 307 keV in the candidate energy spectrum. The processing device 120 may determine a first reference peak position corresponding to 202 keV, and a second reference peak position corresponding to 307 keV particles in the reference energy spectrum. The processing device 120 may determine a first distance between the first reference peak position and the second reference peak position. The processing device 120 may determine a second distance between the first candidate peak position and the second candidate peak position. The processing device 120 may determine whether a difference between the first distance and the second distance is greater than a distance threshold. In response to determining that the difference between the first distance and the second distance is greater than the distance threshold, the processing device 120 may determine that the energy correction state is abnormal, and the energy state of the crystal of the PET device needs to be corrected.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

27

What is claimed is:

1. A method for correcting a positron emission tomography (PET) device, which is implemented on a computing device including at least one processor and at least one storage device, comprising:

obtaining data associated with coincidence events related to intrinsic background radiations of a plurality of crystals of the PET device, wherein each of the coincidence events is detected by two crystals of the plurality of crystals of the PET device, the data associated with each coincidence event includes first time information and second time information, the each coincidence event includes a β event and a γ event, the first time information corresponds to the β event, and the second time information corresponds to the γ event, wherein the obtaining data associated with coincidence events comprises:

obtaining the data associated with the coincidence events based on a target energy window and a target time window, wherein the target energy window is determined based on at least one of a β particle energy, a γ particle energy, or a reference energy, and the target time window is determined based on a reference time;

determining a first time of flight (TOF) difference corresponding to the each coincidence event based on the first time information and the second time information;

determining a second TOF difference corresponding to the each coincidence event based on locations of the two crystals that detect the each coincidence event; and correcting the PET device based on the first TOF difference and the second TOF difference.

2. The method of claim 1, wherein the obtaining data associated with coincidence events comprises:

for the each coincidence event, obtaining a first optical signal excited by a β particle and a second optical signal excited by a γ particle;

obtaining a first electric signal by converting the first optical signal;

obtaining a second electric signal by converting the second optical signal;

determining the first time information based on the first electric signal; and determining the second time information based on the second electric signal.

3. The method of claim 1, wherein a first crystal of the two crystals detects a β particle, and a second crystal of the two crystals detects a γ particle, and the determining a second TOF difference corresponding to the each coincidence event based on locations of the two crystals comprises:

determining the second TOF difference based on a distance between the location of the first crystal and the location of the second crystal.

4. The method of claim 3, wherein the determining the second TOF difference based on a distance between the location of the first crystal and the location of the second crystal comprises:

determining the second TOF difference by dividing the distance between the location of the first crystal and the location of the second crystal by a speed of light.

5. The method of claim 3, wherein a first detector including the first crystal and a second detector including the second crystal are spaced apart from each other.

6. The method of claim 1, wherein the correcting the PET device based on the first TOF difference and the second TOF difference comprises:

for each crystal of the plurality of crystals of the PET device, generating a time spectrum based on the first TOF difference and the second TOF difference corresponding to each of one or more of the coincidence events detected between the crystal and other crystals; and determining a TOF correction value based on the time spectrum; and correcting the PET device based on the TOF correction value corresponding to the each crystal of the plurality of crystals of the PET device.

7. The method of claim 6, wherein the for each crystal of the plurality of crystals of the PET device, determining a TOF correction value based on the time spectrum comprises:

determining the TOF correction value based on the time spectrum according to an iterative operation including one or more iterations, and in at least one of the one or more iterations, the method further comprises:

for the each crystal of the plurality of crystals of the PET device, generating a time spectrum of the crystal; and determining an offset value for the crystal based on the time spectrum;

determining whether the iterative operation satisfies a condition based on the offset value for the crystal; and in response to a result of determining whether the iterative operation satisfies the condition, adjusting TOF information of the crystal based on the offset value for the crystal, or determining the TOF correction value for the crystal by summing one or more offset values for the crystal in the one or more iterations.

8. The method of claim 6, wherein the correcting the PET device based on the TOF correction value corresponding to the each crystal of the plurality of crystals of the PET device comprises:

recording the TOF correction value in a correction file of the PET device, or programming the TOF correction value in one or more detectors of the PET device.

9. The method of claim 1, further comprising:

performing a time walk effect correction and/or a position correction on the first TOF difference.

10. The method of claim 1, further comprising:

correcting the PET device based on energy information of the data associated with the coincidence events.

11. The method of claim 10, wherein the correcting the PET device based on the energy information of the data associated with the coincidence events comprises:

generating a reference energy spectrum based on energy information of the each coincidence event;

determining a reference peak position in the reference energy spectrum;

determining a target peak position based on the reference peak position in the reference energy spectrum; and correcting the PET device based on the target peak position and a corrected peak position.

12. The method of claim 11, wherein the correcting the PET device based on the target peak position and a corrected peak position comprises:

determining whether the PET device needs to be corrected based on the target peak position and the corrected peak position;

in response to determining that the PET device needs to be corrected, programming the target peak position in one or more detectors of the PET device.

13. The method of claim 11, wherein the determining a target peak position based on the reference peak position in the reference energy spectrum comprises:

determining the target peak position based on the reference peak position and a relationship between a position of a peak and an energy of the peak.

14. A system for correcting a positron emission tomography (PET) device, comprising:

at least one storage device including a set of instructions; and at least one processor configured to communicate with the at least one storage device, wherein when executing the set of instructions, the at least one processor is configured to direct the system to perform operations including:

obtaining data associated with coincidence events related to intrinsic background radiations of a plurality of crystals of the PET device, wherein each of the coincidence events is detected by two crystals of the plurality of crystals of the PET device, and the data associated with each coincidence event includes first time information and second time information;

determining a first time of flight (TOF) difference corresponding to the each coincidence event based on the first time information and the second time information;

determining a second TOF difference corresponding to the each coincidence event based on locations of the two crystals that detect the each coincidence event;

correcting the PET device based on the first TOF difference and the second TOF difference;

generating a reference energy spectrum based on energy information of the each coincidence event;

determining a reference peak position in the reference energy spectrum;

determining a target peak position based on the reference peak position in the reference energy spectrum; and correcting the PET device based on the target peak position and a corrected peak position.

15. The system of claim 14, wherein the correcting the PET device based on the first TOF difference and the second TOF difference comprises:

for each crystal of the plurality of crystals of the PET device, generating a time spectrum based on the first TOF difference and the second TOF difference corresponding to each of one or more of the coincidence events detected between the crystal and other crystals; and determining a TOF correction value based on the time spectrum; and correcting the PET device based on the TOF correction value corresponding to the each crystal of the plurality of crystals of the PET device.

16. The system of claim 15, wherein the for each crystal of the plurality of crystals of the PET device, determining a TOF correction value based on the time spectrum comprises:

determining the TOF correction value based on the time spectrum according to an iterative operation including one or more iterations, and in at least one of the one or more iterations, the method further comprises:

for the each crystal of the plurality of crystals of the PET device, generating a time spectrum of the crystal; and determining an offset value for the crystal based on the time spectrum;

determining whether the iterative operation satisfies a condition based on the offset value for the crystal; and in response to a result of determining whether the iterative operation satisfies the condition based on the offset value for the crystal, adjusting TOF information of the crystal based on the offset value for the crystal, or determining the TOF correction value for the crystal by summing one or more offset values for the crystal in the one or more iterations.

17. A method for correcting a positron emission tomography (PET) device, which is implemented on a computing device including at least one processor and at least one storage device, comprising:

obtaining data associated with coincidence events related to intrinsic background radiations of a plurality of crystals of the PET device, wherein each of the coincidence events is detected by two crystals of the plurality of crystals of the PET device, and the data associated with each coincidence event includes first time information and second time information;

determining a first time of flight (TOF) difference corresponding to the each coincidence event based on the first time information and the second time information;

performing a time walk effect correction and/or a position correction on the first TOF difference;

determining a second TOF difference corresponding to the each coincidence event based on locations of the two crystals that detect the each coincidence event; and correcting the PET device based on the first TOF difference and the second TOF difference.

18. The method of claim 17, further comprising:

correcting the PET device based on energy information of the data associated with the coincidence events.

19. The method of claim 18, wherein the correcting the PET device based on the energy information of the data associated with the coincidence events comprises:

generating a reference energy spectrum based on energy information of each coincidence event;

determining a reference peak position in the reference energy spectrum;

determining a target peak position based on the reference peak position in the reference energy spectrum; and correcting the PET device based on the target peak position and a corrected peak position.

20. The method of claim 19, wherein the correcting the PET device based on the target peak position and a corrected peak position comprises:

determining whether the PET device needs to be corrected based on the target peak position and the corrected peak position;

in response to determining that the PET device needs to be corrected, programming the target peak position in one or more detectors of the PET device.

* * * * *